United States Patent
Manzotti et al.

(10) Patent No.: US 8,754,212 B2
(45) Date of Patent: Jun. 17, 2014

(54) PROCESS FOR THE PREPARATION OF STABLE, AMORPHOUS CALCIUM SALT OF (6S)-N(5)-METHYL-5,6,7,8-TETRAHYDROFOLIC ACID

(75) Inventors: Raffella Manzotti, Pellio Intelvi (IT); Moreno Morosoli, Tesserete (CH)

(73) Assignee: Cerbios-Pharma S.A., Barbengo (CH)

( * ) Notice: Subject to any disclaimer, the term of this patent is extended or adjusted under 35 U.S.C. 154(b) by 0 days.

(21) Appl. No.: 13/585,627

(22) Filed: Aug. 14, 2012

(65) Prior Publication Data

US 2013/0040956 A1  Feb. 14, 2013

Related U.S. Application Data

(63) Continuation of application No. 12/601,207, filed as application No. PCT/CH2008/000242 on May 29, 2008, now Pat. No. 8,314,102.

(30) Foreign Application Priority Data

May 30, 2007 (CH) ......................................... 856/07

(51) Int. Cl.
  *C07D 475/04* (2006.01)
(52) U.S. Cl.
  USPC ........................................................ 544/258
(58) Field of Classification Search
  CPC ..................................................... C07D 475/04
  USPC ........................................................ 544/258
  See application file for complete search history.

(56) References Cited

U.S. PATENT DOCUMENTS

| | | |
|---|---|---|
| 5,194,611 A | 3/1993 | Marazza et al. |
| 5,324,836 A | 6/1994 | Müller et al. |
| 5,457,202 A | 10/1995 | Scheib et al. |
| 6,441,168 B1 | 8/2002 | Müller et al. |

FOREIGN PATENT DOCUMENTS

| | | |
|---|---|---|
| EP | 0 455 013 A1 | 11/1991 |
| EP | 1 044 975 A1 | 10/2000 |
| WO | WO9310118 | 5/1993 |

OTHER PUBLICATIONS

International Search Report for PCT/CH2008/000242, mailed Jul. 30, 2008.

*Primary Examiner* — Douglas M Willis
(74) *Attorney, Agent, or Firm* — Buchanan Ingersoll & Rooney PC

(57) ABSTRACT

A process for the preparation of the stable, amorphous calcium salt of (6S)—N(5)-methyl-5,6,7,8-tetrahydrofolic acid of the formula V, Formula V

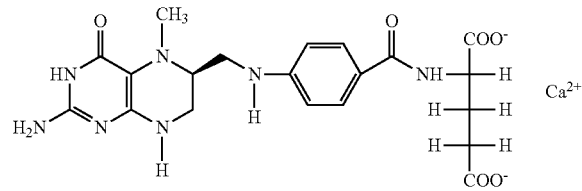

and a stable, amorphous calcium salt of (6S)—N(5)-methyl-5,6,7,8-tetrahydrofolic acid of the formula V are provided.

4 Claims, 6 Drawing Sheets

| Pos.[°2Th.] | Height[cts] | FWHM[°2Th.] | d-spacing[Å] | Rel.Int.[%] |
|---|---|---|---|---|
| 9.3431 | 359.62 | 0.0836 | 9.46587 | 2.73 |
| 11.8681 | 2647.01 | 0.1171 | 7.45705 | 20.13 |
| 12.3773 | 1821.97 | 0.1171 | 7.15137 | 13.85 |
| 13.0412 | 401.95 | 0.1171 | 6.78879 | 3.06 |
| 15.0256 | 3901.81 | 0.1673 | 5.89638 | 29.67 |
| 15.5983 | 4007.87 | 0.1506 | 5.68114 | 30.47 |
| 16.2341 | 654.91 | 0.0669 | 5.46005 | 4.98 |
| 16.5335 | 1150.34 | 0.1338 | 5.36185 | 8.75 |
| 17.4160 | 4331.05 | 0.1506 | 5.09210 | 32.93 |
| 18.4448 | 951.34 | 0.1171 | 4.81033 | 7.23 |
| 18.7080 | 3064.94 | 0.1506 | 4.74324 | 23.30 |
| 19.9280 | 4004.29 | 0.1506 | 4.45553 | 30.45 |
| 20.1856 | 1379.90 | 0.1004 | 4.39924 | 10.49 |
| 20.5606 | 181.70 | 0.1004 | 4.31984 | 1.38 |
| 22.1764 | 13152.35 | 0.1673 | 4.00862 | 100.00 |
| 22.4365 | 3415.42 | 0.1004 | 3.96273 | 25.97 |
| 23.3256 | 1040.66 | 0.1171 | 3.81365 | 7.91 |
| 23.8520 | 1007.47 | 0.1224 | 3.72759 | 7.66 |
| 23.9477 | 901.13 | 0.0816 | 3.72213 | 6.85 |
| 24.3286 | 4533.85 | 0.2040 | 3.65564 | 34.47 |
| 24.8526 | 1398.77 | 0.1632 | 3.57973 | 10.64 |
| 25.0754 | 450.57 | 0.1020 | 3.54842 | 3.43 |
| 25.3878 | 821.59 | 0.2244 | 3.50547 | 6.25 |
| 25.7370 | 319.21 | 0.1224 | 3.45869 | 2.43 |
| 26.6345 | 568.65 | 0.1632 | 3.34414 | 4.32 |
| 27.4247 | 511.56 | 0.0816 | 3.24956 | 3.89 |
| 27.6955 | 634.16 | 0.1224 | 3.21839 | 4.82 |
| 28.4575 | 553.70 | 0.2040 | 3.13392 | 4.21 |
| 28.8157 | 980.98 | 0.1836 | 3.09577 | 7.46 |
| 29.4988 | 3680.74 | 0.2448 | 3.02563 | 27.99 |
| 30.1602 | 898.39 | 0.1224 | 2.96076 | 6.83 |
| 30.4262 | 1440.45 | 0.1632 | 2.93548 | 10.95 |
| 31.3576 | 124.72 | 0.1632 | 2.85038 | 0.95 |
| 32.8840 | 117.00 | 0.1632 | 2.72147 | 0.89 |
| 33.7872 | 501.16 | 0.1632 | 2.65076 | 3.81 |
| 34.5202 | 607.26 | 0.1428 | 2.59614 | 4.62 |
| 34.8769 | 250.91 | 0.1224 | 2.57039 | 1.91 |
| 35.2871 | 275.14 | 0.1632 | 2.54145 | 2.09 |
| 35.8915 | 432.75 | 0.3672 | 2.50003 | 3.29 |
| 36.2611 | 305.22 | 0.2040 | 2.47539 | 2.32 |
| 36.5806 | 123.96 | 0.1224 | 2.45449 | 0.94 |
| 37.5778 | 586.47 | 0.2448 | 2.39162 | 4.46 |
| 38.2761 | 209.70 | 0.1428 | 2.34958 | 1.59 |

Fig 3b

PROCESS FOR THE PREPARATION OF STABLE, AMORPHOUS CALCIUM SALT OF (6S)-N(5)-METHYL-5,6,7,8-TETRAHYDROFOLIC ACID

CROSS-REFERENCE TO RELATED APPLICATION

This application is a continuation of U.S. patent application Ser. No. 12/601,207, filed on Nov. 20, 2009, now U.S. Pat. No. 8,314,102 which is a National Stage of PCT/CH2008/000242, filed on May 29, 2008, which claims priority to Switzerland Application No. 856/07, filed May 30, 2007, the entire content of each is hereby incorporated by reference.

BACKGROUND

The present invention is directed to a process for the preparation of the stable, amorphous calcium salt of (6S)—N(5)-methyl-5,6,7,8-tetrahydrofolic acid of the formula V.

The present invention is also directed to a process for the preparation of stable, crystalline (6S)-N(5)-methyl-5,6,7,8-tetrahydrofolic acid of the formula IV.

The present invention is also directed to a process for the preparation of an aqueous solution of the calcium salt of (6S)—N(5)-methyl-5,6,7,8-tetrahydrofolic acid of the formula III.

In the present invention for 5,6,7,8-tetrahydrofolic acid is used sometimes the abbreviation THF.

A short summary concerning the pharmacological importance of N(5)-methyl-5,6,7,8-tetrahydrofolic acid—herein sometimes abbreviated with N(5)-methyl-THF—and derivatives thereof is given in the beginning of the description of EP 0 455 013 A1. In the same document is also pointed to the importance of the individual (6S)- and (6R)-diastereoisomers of N(5)-methyl-THF. Herein is also described the prior art concerning the preparation of the pure (6S)- and (6R)-diastereoisomers of N(5)-methyl-THF.

In EP 1 044 975 A1 are described stable crystalline salts of N(5)-methyl-THF. Herein are also described crystalline calcium salts of (6S)—N(5)-methyl-THF, whereby these salts have in the respective X-ray powder diffraction diagram well defined 2-Theta-values.

In the preparation process of these salts are used as starting materials either the mixture of the (6RS)-diastereoisomers or the already separated (6S)- or (6R)-diastereoisomers. This process involves a temperature treatment of more than 60° C., preferably of more than 85° C., whereby in the working examples are mentioned temperatures from 90° C. to 100° C.

Such a temperature treatment is of course less suitable for an industrial preparation of these salts.

In EP 1 044 975 A1 is not mentioned by what way the individual (6S)- or (6R)-diastereoisomers of N(5)-methyl-THF were obtained.

SUMMARY OF SELECTED FEATURES

It is an object of the present invention to provide an industrially applicable process for the preparation of a stable calcium salt of (6S)—N(5)-methyl-5,6,7,8-tetrahydrofolic acid of the formula V.

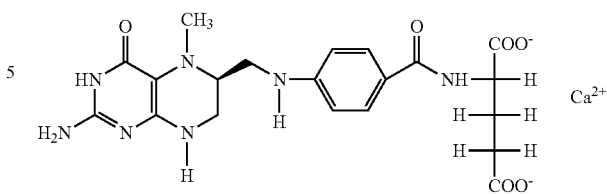

Formula V

The product obtainable with this process shall have a diastereoisomeric purity of at least 99%.

This process shall be simple and shall especially not involve a thermal treatment.

It is a further object of the present invention to provide a process for the preparation of stable, crystalline (6S)—N(5)-methyl-5,6,7,8-tetrahydrofolic acid of the formula IV.

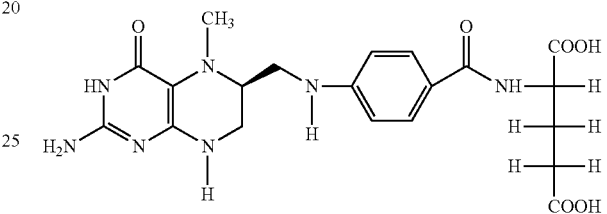

Formula IV

It is a further object of the present invention to provide a process for the preparation of an aqueous solution of the calcium salt of (6S)—N(5)-methyl-5,6,7,8-tetrahydrofolic acid of the formula III. With this process shall be obtained an aqueous solution of the calcium salt of N(5)-methyl-THF, in which the (6S)-diastereoisomer is highly enriched 98%).

With the present invention are met these objectives.

The inventive process for the preparation of an aqueous solution of the calcium salt of (6S)—N(5)-methyl-5,6,7,8-tetrahydrofolic acid of the formula III,

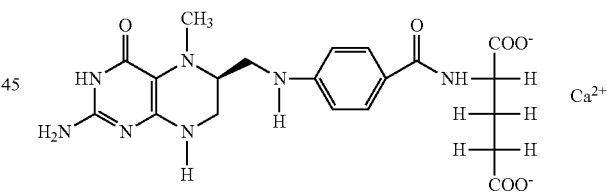

Formula III whereby (6S)-5,6,7,8-tetrahydrofolic acid of the formula II

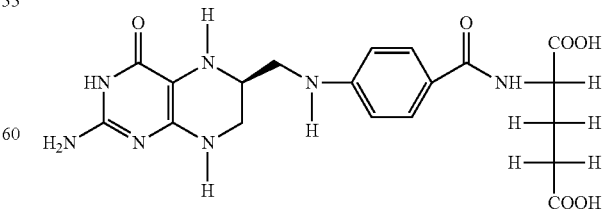

Formula II having a content of the corresponding (6R)-diastereoisomer in the range from 4% by weight to 8% by weight is methylated in water, is characterized in that to the obtained methylated reaction mixture are added from 0.70 to 0.82 equivalents, referred to the used amount of THF, of calcium chloride, from the so obtained aqueous solution the calcium salt of (6RS)—N(5)-methyl-5,6,7,8-tetrahydrofolic acid is selectively crystallized and separated, and the aqueous solution of the calcium salt of (6S)—N(5)-methyl-5,6,7,8-tetrahydrofolic acid of the formula III having a content of the corresponding (6R)-diastereoisomer of ≤2% by weight is obtained.

The inventive process for the preparation of stable, crystalline (6S)—N(5)-methyl-5,6,7,8-tetrahydrofolic acid of the formula IV is characterized in that to an aqueous solution of the calcium salt of (6S)—N(5)-methyl-5,6,7,8-tetrahydrofolic acid of the formula III having a content of the corresponding (6R)-diastereoisomer of 2% by weight is added either acetic acid or a sulfonic acid in such an amount, until a pH-value of 5.5 is obtained, the so obtained solution is warmed to a temperature in the range from 44° C. to 46° C., to this warmed solution is added either acetic acid or a sulfonic acid in such an amount, until a pH-value in the range from 4.3 to 4.4 is obtained, whereby the crystallization of (6S)—N(5)-methyl-5,6,7,8-tetrahydrofolic acid of the formula IV begins, whereby during this crystallization the pH-value is maintained in the range from 4.3 to 4.4 by continuous addition of either acetic acid or of a sulfonic acid, and the so obtained crystalline solid is filtered off at a temperature in the range from 44° C. to 46° C. and is isolated.

The inventive process for the preparation of the stable, amorphous calcium salt of (6S)—N(5)-methyl-5,6,7,8-tetrahydrofolic acid of the formula V is characterized in that crystalline (6S)—N(5)-methyl-5,6,7,8-tetrahydrofolic acid of the formula IV, prepared according to the process described herein, is suspended in water, whereby the water has a temperature from 35° C. to 41° C., to this suspension is added a NaOH solution in portions and in such an amount until a pH-value in the range from 6.7 to 6.9 is obtained, to the so prepared solution are added 0.90 equivalents of calcium chloride, referred to the used amount of the compound of formula IV, in the so prepared solution the concentration of the compound of formula IV is adjusted either by the addition or by the removal of water to a value in the range from 14% by weight to 16% by weight, the precipitation of the calcium salt of (6S)—N(5)-methyl-5,6,7,8-tetrahydrofolic acid of the formula V is started by the addition of a small amount of previously prepared compound of formula V, the so prepared mixture is kept during 1 hour at a temperature of 40° C., then within 2 hours the temperature is lowered from 40° C. to a temperature of 23° C., said temperature of 23° C. is maintained during 16 to 18 hours, and the obtained solid is isolated.

Preferred embodiments of the present invention are defined in the dependent claims.

In the following part are described possible embodiments of the present invention.

Thereby reference is also made to the Figures.

BRIEF DESCRIPTION OF THE DRAWINGS

FIG. 3b shows the 2 Theta-values having an error of about ±0.2 degree of the in FIG. 3a shown X-ray powder diffraction diagram.

DETAILED DESCRIPTION (6S)-5,6,7,8-tetrahydrofolic acid of the formula II having a content of the corresponding (6R)-diastereoisomer in the range from 4% by weight to 8% by weight was prepared according to EP 0 600 460.

It was quite surprising that one could obtain an aqueous solution of the calcium salt of (6S)—N(5)-methyl-5,6,7,8-tetrahydrofolic acid of the formula III with an increased content of the (6S)-isomer by selectively crystallizing out from the solution the 1:1 mixture of the diastereoisomeric salts.

Routinely one could isolate a solution having a content of the (6S)-isomer of at least 98%.

It was also quite surprising to obtain the corresponding stable, crystalline free acid of formula IV from the above described solution: moreover during this step a further increase of the diastereoisomeric purity of at least 99% was achieved.

The stable, crystalline (6S)—N(5)-methyl-5,6,7,8-tetrahydrofolic acid of the formula IV could be isolated in such a diastereoisomeric purity that this acid may be used as at least one active component in a dietary supplement or in a medicament.

From the acid of the formula IV is prepared the surprisingly stable, amorphous calcium salt of the formula V.

Figure 5:
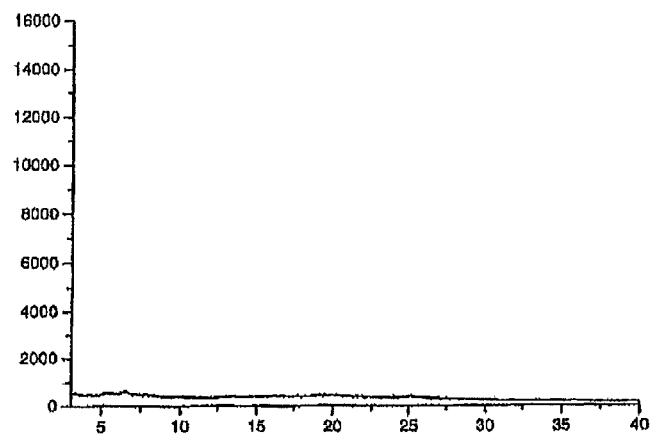
FIG. 5 shows the X-ray powder diffraction diagram of the compound of formula V. On the abscissa are plotted the 2 Theta-values, and on the ordinate is plotted the intensity (counts).

It is obvious from the X-ray powder diffraction diagram of the compound of formula V—see FIG. 5—that this compound is practically amorphous.

The present invention is illustrated by the following examples.

Example 1

Preparation of the Aqueous sSolution of the Calcium Salt of (6S)—N(5)-methyl-5,6,7,8-tetrahydrofolic Acid of the Formula III 100 g of (6S)-5,6,7,8-tetrahydrofolic acid of the formula II having a diastereoisomeric purity of (6S):(6R) of 92:8—prepared according to EP 0 600 460—were suspended in water having a temperature of 7° C. under a nitrogen atmosphere.

The compound of formula II was dissolved by the addition of 65 ml of 20% (w/w) aqueous NaOH solution. The pH-value was then 9.05.

To this solution were added 23.7 g of 36% (w/w) aqueous formaldehyde solution within 5 minutes at a temperature of 8° C. under stirring.

After 15 minutes was added an aqueous $NaBH_4$-solution, prepared by dissolving of 21.3 g of $NaBH_4$ in 50 ml of water and 1 ml of 20% (w/w) aqueous NaOH solution, during 1 hour at a temperature of 8° C. under stirring.

This mixture was stirred during 30 minutes at a temperature of 8° C. and then during 20 minutes at a temperature of 61° C.

The reaction temperature was then lowered within 2 hours to 20° C.

Then were added dropwise 79 ml of 18% (w/w) aqueous HCl solution. The pH-value was then 8.03.

The mixture was cooled to a temperature of 4° C. in order to allow the borate precipitation. After 2 hours the borates were removed by filtration.

The pH-value of the resulting solution was adjusted by the addition of 10 ml of 18% (w/w) aqueous HCl solution to a value of 7.03.

This solution was warmed to a temperature of 20° C., and then were added first 1.62 g of di-sodium-EDTA and then 0.82 equivalents (25.44 g) of $CaCl_2.2H_2O$.

Then the pH-value was adjusted to a value of 6.9 by the addition of 2 ml of 20% (w/w) aqueous NaOH solution.

The selective crystallization of the calcium salt of (6RS)—N(5)-methyl-5,6,7,8-tetrahydrofolic acid was realized by seeding the solution with 100 mg of previously prepared crystals of the calcium salt of (6RS)—N(5)-methyl-5,6,7,8-tetrahydrofolic acid, followed by a lowering of the temperature from room temperature to a temperature of 4° C. within 40 minutes.

The resulting suspension was kept under stirring during 18 hours at a temperature of 4° C.

The obtained crystals were filtered off.

The so obtained aqueous solution of the calcium salt of (6S)—N(5)-methyl-5,6,7,8-tetrahydrofolic acid of the formula III had a content of the corresponding (6R)-diastereoisomer of 2% by weight, as shown by HPLC on a chiral column.

Example 2

Preparation of Crystalline (6S)-N(5)-methyl-5,6,7,8-tetrahydrofolic Acid of the Formula IV To the aqueous solution of the calcium salt of (6S)—N(5)-methyl-5,6,7,8-tetrahydrofolic acid of the formula III having a content of the corresponding (6R)-diastereoisomer of ≤2% by weight, prepared according to the above example 1, were added within 20 minutes 6 ml of 100% acetic acid until a pH-value of 5.5 was obtained.

Then the temperature was raised to 45° C.

At this temperature were added consecutively 1.35 g of sodium-dithionite and 1.9 g of di-sodium-EDTA.

To this solution were added 25 ml of 100% acetic acid within 15 minutes.

At a pH-value of 4.5 started the crystallization of (6S)—N(5)-methyl-5,6,7,8-tetrahydrofolic acid of the formula IV.

The pH-value was kept in the range from 4.3 to 4.4 by continuous addition of 100% acetic acid (10 ml).

This suspension was stirred during 30 minutes and was then filtered off.

The so obtained crystalline solid was washed with water having a temperature of 40° C.

There were obtained 106.9 g of wet crystalline solid.

For the determination of the purity and of the ratio of the diastereoisomers a sample of the compound of formula IV was washed with 94% (v/v) aqueous ethanol and was then dried under reduced pressure. Thereby the following results were obtained:

HPLC purity: 96.45%

Ratio of (6S)/(6R)=99.1:0.9 (determined by chiral HPLC).

The so obtained product of formula IV had the following stability data (stored at a temperature of 4° C.)

| Time (months) | HPLC purity (%) |
| --- | --- |
| 0 | 96.45 |
| 6 | 96.66 |

Example 3

Preparation of the Amorphous Calcium Salt of (6S)—N(5)-methyl-5,6,7,8-tetrahydrofolic Acid of the Formula V 106.9 g of wet crystalline solid, prepared according to the above example 2, were suspended in 400 ml of water having a temperature of 40° C.

To this suspension were added slowly 65 ml of 20% (w/w) aqueous NaOH solution, until a clear solution having a pH-value of 6.8 was obtained.

To this solution were added 0.90 equivalents of $CaCl_2.2H_2O$ (22.7 g, referred to the amount of isolated dry compound of formula IV).

The HPLC determination of (6S)—N(5)-methyl-5,6,7,8-tetrahydrofolic acid gave a concentration in solution of c=14.7% w/w.

The pH-value was adjusted to a value of 6.8 by the addition of 1 ml of 20% (w/w) aqueous NaOH solution.

The precipitation of the calcium salt of (6S)-N(5)-methyl-5,6,7,8-tetrahydrofolic acid of the formula V was started by the addition of 100 mg of previously prepared compound of formula V.

The so prepared mixture was kept during 1 hour at a temperature of 40° C.

Then within 2 hours the temperature of 40° C. was lowered to a temperature of 23° C., and the temperature of 23° C. was maintained during 18 hours.

When the concentration of the calcium salt of (6S)—N(5)-methyl-5,6,7,8-tetrahydrofolic acid of the formula V in the mother liquor was below 7.5% then the suspension was filtered off.

The obtained solid was washed with 50 ml of water having a temperature of 10° C.

The wet compound of formula V was suspended in 250 ml of 94% (v/v) aqueous ethanol at a temperature of 22° C. and was stirred during 30 minutes.

Then this suspension was filtered off and was washed twice with 50 ml 94% (v/v) aqueous ethanol.

There were obtained 95 g of a wet solid which was dried under reduced pressure. There were obtained 47.3 g of the compound of formula V.

Thereby the following analytical data were obtained:
HPLC purity: 98.75%
Ratio of (6S)/(6R)=99.75:0.25 (determined by chiral HPLC).

The so obtained product of formula V had the following stability data (stored at a temperature of 25° C. under vacuum [2 mbar]):

| Time (months) | HPLC assay (%) | HPLC purity (%) |
|---|---|---|
| 0 | 99.0 | 98.7 |
| 1 | 98.8 | 98.7 |
| 2 | 99.8 | 98.9 |
| 3 | 100.2 | 98.8 |
| 6 | 99.9 | 98.5 |
| 9 | 100.7 | 98.9 |

We claim:

1. A calcium salt of (6S)—N(5)-methyl-5,6,7,8-tetrahydrofolic acid of the Formula V Formula V prepared by:
(a) adding to an aqueous solution of the calcium salt of (6S)—N(5)-methyl-5,6,7,8-tetrahydrofolic acid of the Formula III

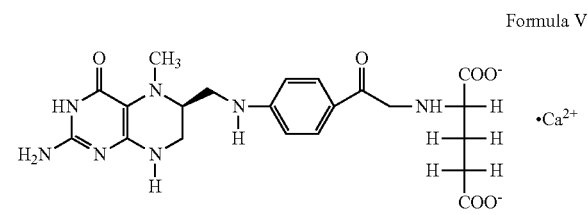

Figure 1:
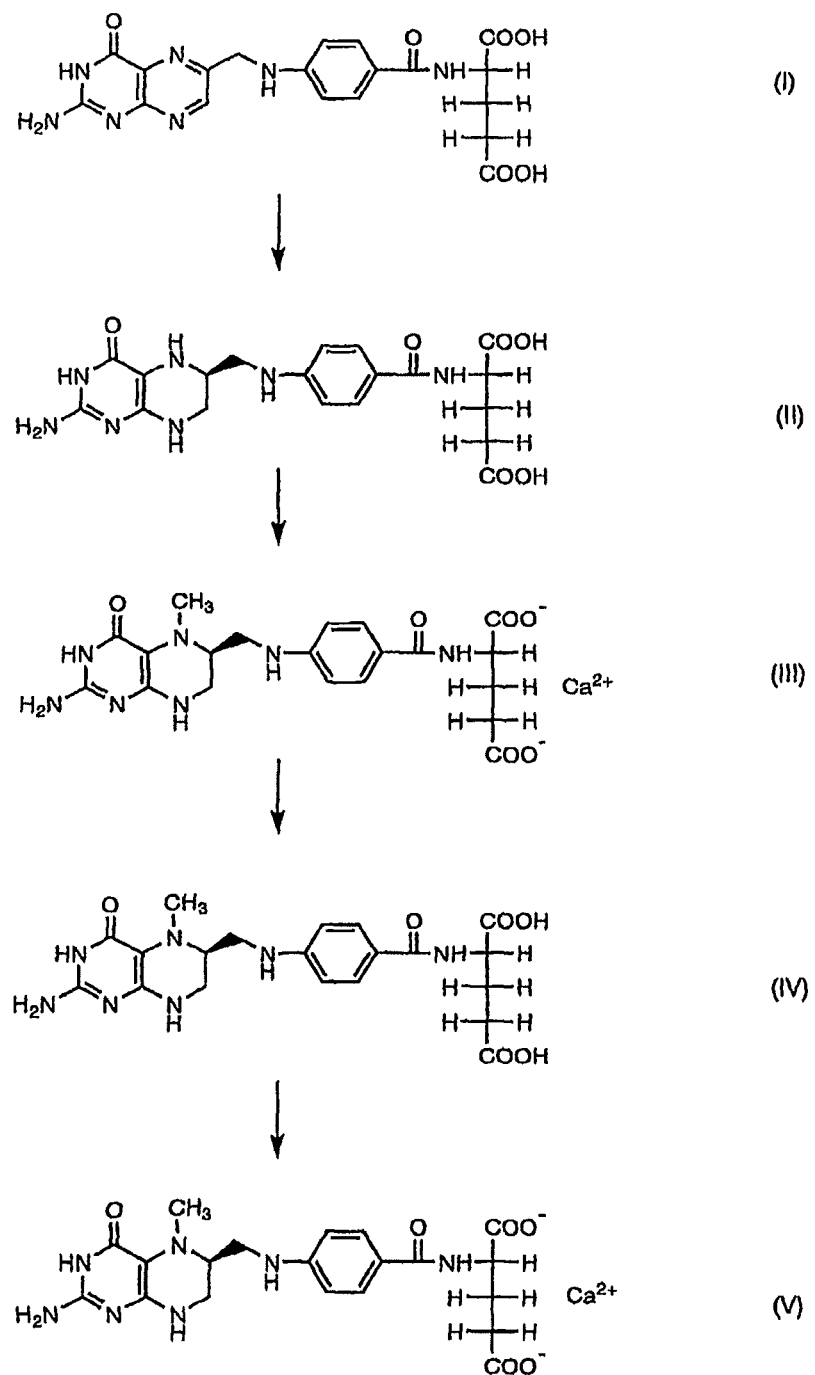
FIG. 1 shows a reaction scheme, starting with the compound of formula I and ending with the compound of formula V.
Figure 2A:
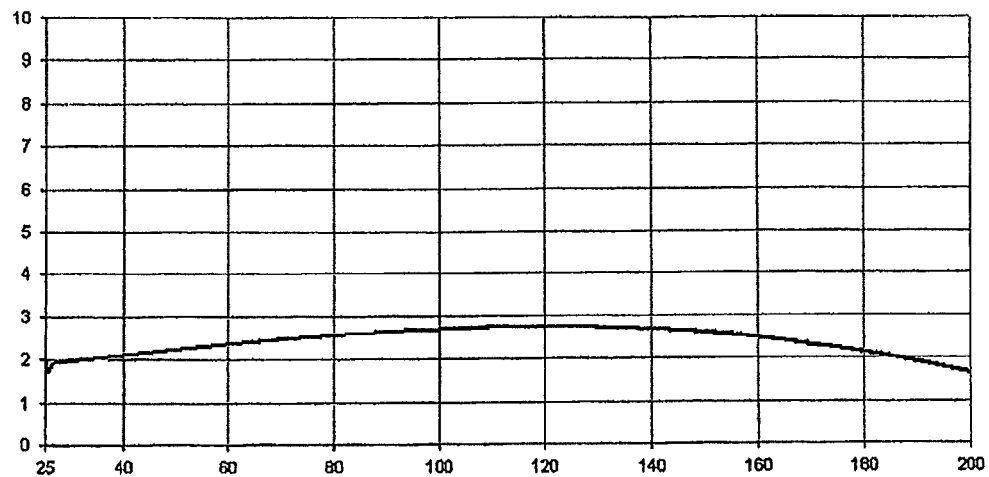
FIG. 2a shows the "differential scanning calorimetric" profile, DSC, of the compound of formula IV. On the abscissa is plotted the temperature in ° C., and on the ordinate is plotted the endothermic heat flow in mW.
Figure 2B:
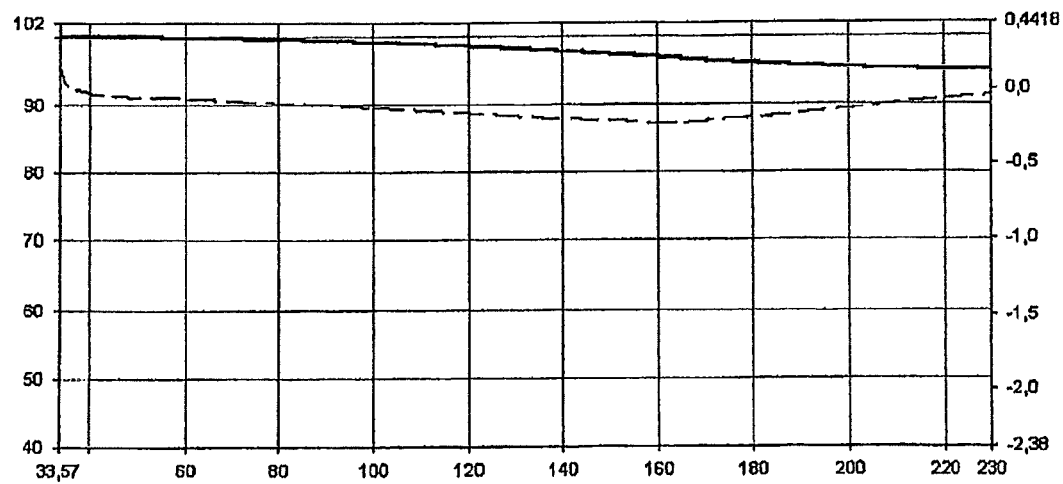
FIG. 2b shows the thermo gravimetric profile, TGA, of the compound of formula IV. On the abscissa is plotted the temperature in ° C. On the left ordinate are plotted percents by weight and on the right ordinate is plotted the derivative of these percents by weight against the time t (minutes). The solid line refers to the left ordinate, and the dotted line refers to the right ordinate.
Figure 3A:
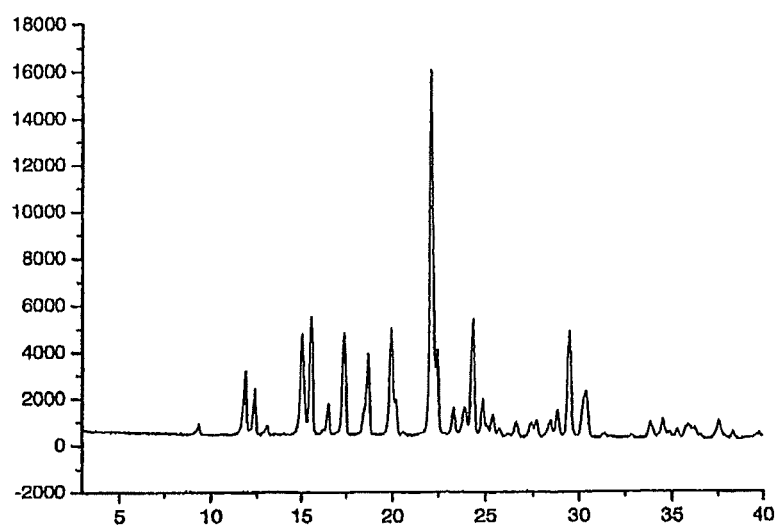
FIG. 3a shows the X-ray powder diffraction diagram of the compound of formula IV. On the abscissa are plotted the 2 Theta-values, and on the ordinate is plotted the intensity (counts).
Figure 4A:
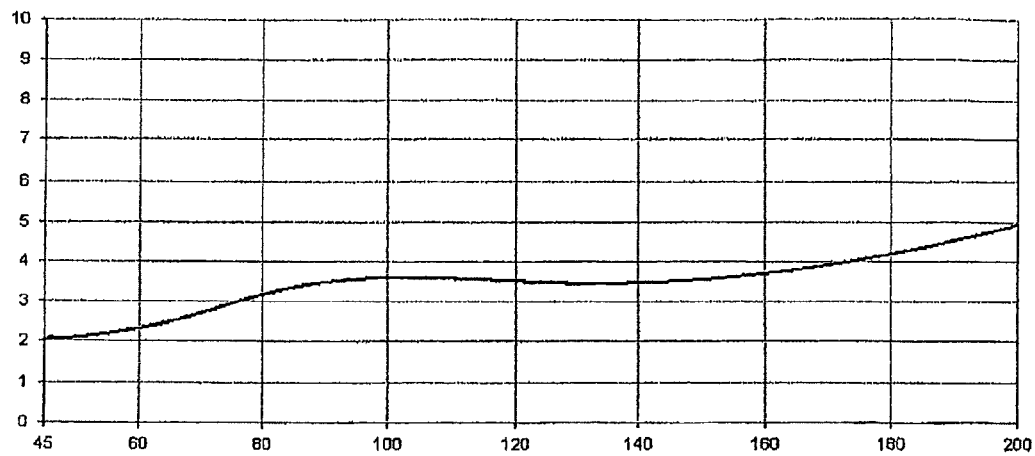
FIG. 4a shows the "differential scanning calorimetric" profile, DSC, of the compound of formula V. On the abscissa is plotted the temperature in ° C., and on the ordinate is plotted the endothermic heat flow in mW.
Figure 4B:
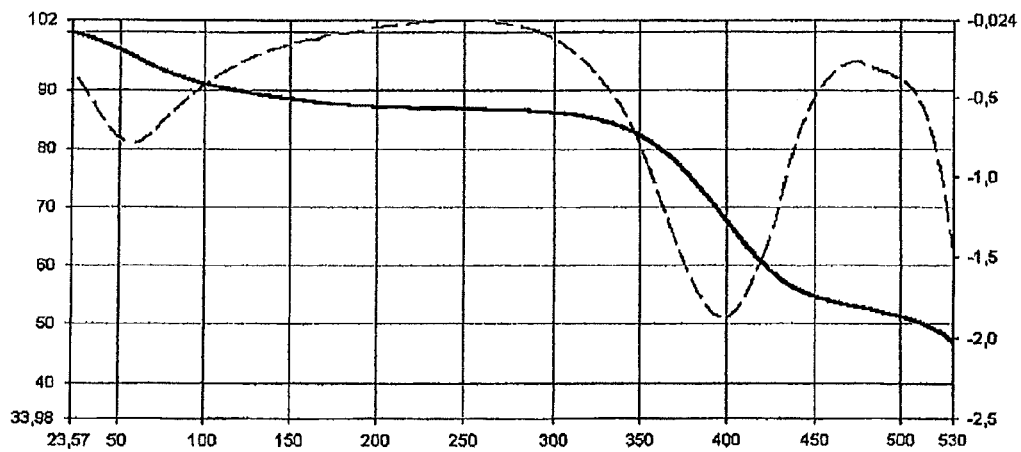
FIG. 4b shows the thermo gravimetric profile, TGA, of the compound of formula V. On the abscissa is plotted the temperature in ° C. On the left ordinate are plotted percents by weight and on the right ordinate is plotted the derivative of these percents by weight against the time t (minutes). The solid line refers to the left ordinate, and the dotted line refers to the right ordinate.
Figure 6:
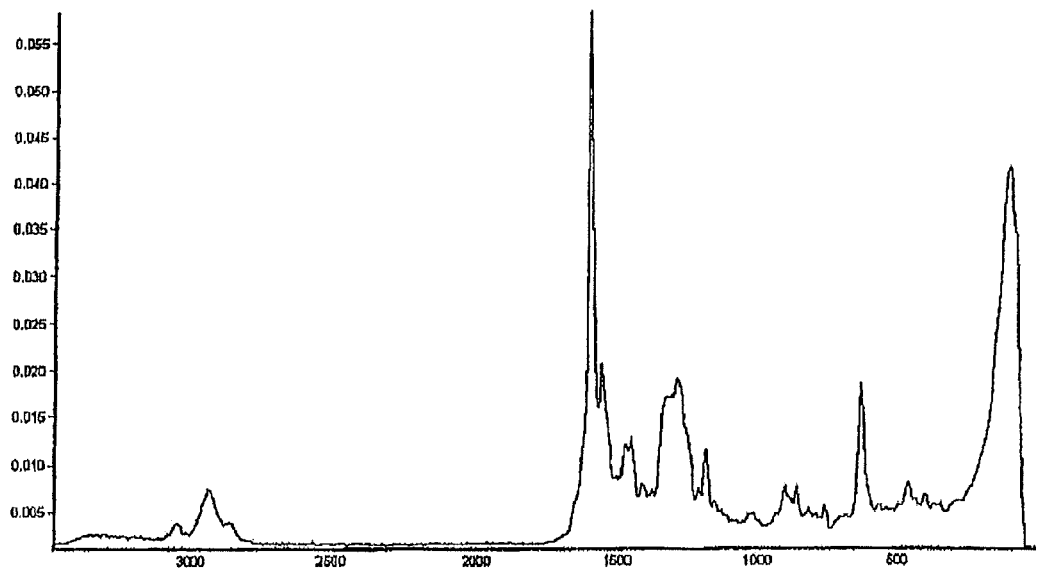
FIG. 6 shows the Raman spectra of the compound of formula V. On the abscissa is plotted the wave number in $cm^{-1}$, and on the ordinate is plotted the Raman intensity.

Formula III having a content of the corresponding (6R)-diastereoisomer of ≤2% by weight either acetic acid or a sulfonic acid in such an amount, until a pH-value of 5.5 is obtained;
(b) warming the resulting solution to a temperature from 44° C. to 46° C.;
(c) adding to the warmed solution either acetic acid or a sulfonic acid in such an amount, until a pH-value in the range from 4.3 to 4.4 is obtained, whereby the crystallization of (6S)—N(5)-methyl-5,6,7,8-tetrahydrofolic acid of the Formula IV Formula IV begins, and whereby during this crystallization the pH-value is maintained in the range from 4.3 to 4.4 by continuous addition of either acetic acid or of a sulfonic acid;
(d) filtering off crystalline (6S)—N(5)-methyl-5,6,7,8-tetrahydrofolic acid of the Formula IV at a temperature in the range from 44° C. to 46° C.;
(e) isolating (6S)—N(5)-methyl-5,6,7,8-tetrahydrofolic acid of the Formula IV;
(f) suspending the (6S)—N(5)-methyl-5,6,7,8-tetrahydrofolic acid of the Formula IV of step (e) in water at a temperature from 35° C. to 41° C.;
(g) continuously adding a sodium hydroxide solution to the aqueous suspension containing (6S)—N(5)-methyl-5,6,7,8-tetrahydrofolic acid of the Formula IV of step (f) to adjust the pH to a range from 6.7 to 6.9;
(h) adding 0.90 equivalents of calcium chloride to the solution of step (g) with respect to each equivalent of (6S)—N(5)-methyl-5,6,7,8-tetrahydrofolic acid of the Formula IV;
(i) adjusting the concentration of the compound of Formula IV in the resulting mixture of step (h) to a value in the range from 14% by weight to 16% by weight by the addition or by removal of water;
(j) starting the precipitation of the calcium salt of (6S)—N(5)-methyl-5,6,7,8-tetrahydrofolic acid of the Formula V from the mixture of step (i) by the addition of a small amount of previously prepared compound of Formula V;
(k) maintaining the mixture of step (j) at a temperature of 40° C. for one hour;
(l) lowering the temperature of the mixture of step (k) from 40° C. to a temperature of 23° C. over two hours;
(m) maintaining the mixture of step (l) at 23° C. for a period of 16 hours to 18 hours; and
(n) isolating the amorphous calcium salt of (6S)—N(5)-methyl-5,6,7,8-tetrahydrofolic acid of the Formula V from the mixture of step (m),
and having:
(i) the differential scanning calorimetric profile of FIG. 4a,
(ii) the thermogravimetric profile of FIG. 4b,
(iii) the X-ray powder diffraction diagram of FIG. 5, and
(iv) the Raman spectrum of FIG. 6.

2. A process for the preparation of the stable, amorphous calcium salt of (6S)—N(5)-methyl-5,6,7,8-tetrahydrofolic acid of Formula V,

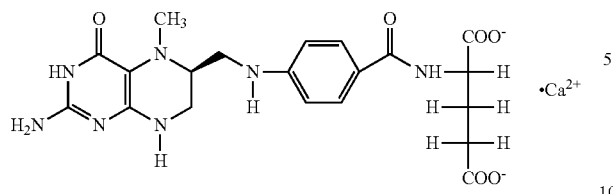

Formula V comprising:
(a) adding to an aqueous solution of the calcium salt of (6S)—N(5)-methyl-5,6,7,8-tetrahydrofolic acid of the Formula III

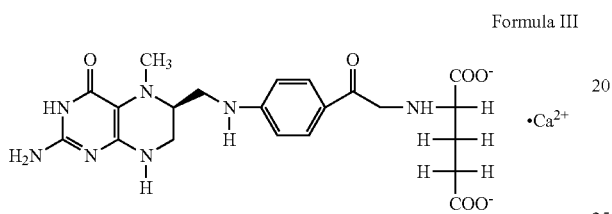

Formula III having a content of the corresponding (6R)-diastereoisomer of ≤2% by weight either acetic acid or a sulfonic acid in such an amount, until a pH-value of 5.5 is obtained;
(b) warming the resulting solution to a temperature from 44° C. to 46° C.;
(c) adding to the warmed solution either acetic acid or a sulfonic acid in such an amount, until a pH-value in the range from 4.3 to 4.4 is obtained, whereby the crystallization of (6S)—N(5)-methyl-5,6,7,8-tetrahydrofolic acid of the Formula IV

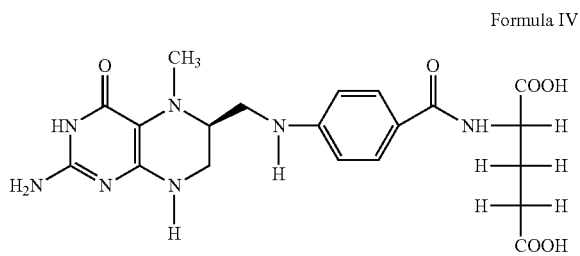 [SMILES: CN1c2c(nc(N)[nH]c2=O)NC[C@@H]1CNc1ccc(C(=O)NC(CCC(=O)O)C(=O)O)cc1]

Formula IV begins, and whereby during this crystallization the pH-value is maintained in the range from 4.3 to 4.4 by continuous addition of either acetic acid or of a sulfonic acid;
(d) filtering off crystalline (6S)—N(5)-methyl-5,6,7,8-tetrahydrofolic acid of the Formula IV at a temperature in the range from 44° C. to 46° C.;
(e) isolating (6S)—N(5)-methyl-5,6,7,8-tetrahydrofolic acid of the Formula IV;
(f) suspending the (6S)—N(5)-methyl-5,6,7,8-tetrahydrofolic acid of the Formula IV of step (e) in water at a temperature from 35° C. to 41° C.;
(g) continuously adding a sodium hydroxide solution to the aqueous suspension containing (6S)—N(5)-methyl-5,6,7,8-tetrahydrofolic acid of the Formula IV of step (f) to adjust the pH to a range from 6.7 to 6.9;
(h) adding 0.90 equivalents of calcium chloride to the solution of step (g) with respect to each equivalent of (6S)—N(5)-methyl-5,6,7,8-tetrahydrofolic acid of the Formula IV;
(i) adjusting the concentration of the compound of Formula IV in the resulting mixture of step (h) to a value in the range from 14% by weight to 16% by weight by the addition or by removal of water;
(j) starting the precipitation of the calcium salt of (6S)—N(5)-methyl-5,6,7,8-tetrahydrofolic acid of the Formula V from the mixture of step (i) by the addition of a small amount of previously prepared compound of Formula V;
(k) maintaining the mixture of step (j) at a temperature of 40° C. for one hour;
(l) lowering the temperature of the mixture of step (k) from 40° C. to a temperature of 23° C. over two hours;
(m) maintaining the mixture of step (l) at 23° C. for a period of 16 hours to 18 hours; and
(n) isolating the amorphous calcium salt of (6S)—N(5)-methyl-5,6,7,8-tetrahydrofolic acid of the Formula V from the mixture of step (m).

3. The process of claim 2, further comprising the steps of:
(o) rinsing the amorphous calcium salt of (6S)—N(5)-methyl-5,6,7,8-tetrahydrofolic acid of the Formula V, obtained in step (n), with water having a temperature of 10° C.;
(p) suspending the amorphous calcium salt of (6S)—N(5)-methyl-5,6,7,8-tetrahydrofolic acid of the Formula V of step (o) in 94% v/v EtOH:H₂O at room temperature; and
(q) filtering off the amorphous calcium salt of (6S)—N(5)-methyl-5,6,7,8-tetrahydrofolic acid of the Formula V from the suspension of step (p).

4. A process for the preparation of the stable, amorphous calcium salt of (6S)—N(5)-methyl-5,6,7,8-tetrahydrofolic acid of Formula V,

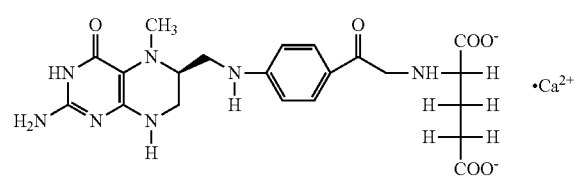

Formula V comprising:
(a) adding to an aqueous solution of the calcium salt of (6S)—N(5)-methyl-5,6,7,8-tetrahydrofolic acid of the Formula III

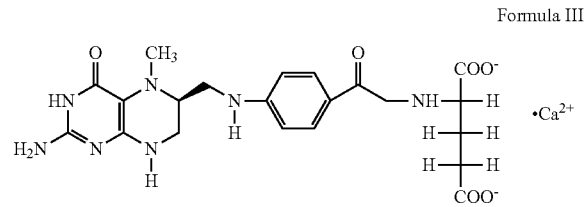

Formula III having a content of the corresponding (6R)-diastereoisomer of ≤2% by weight either acetic acid or a sulfonic acid in such an amount, until a pH-value of 5.5 is obtained;
(b) warming the resulting solution to a temperature from 44° C. to 46° C.;
(c) adding to the warmed solution either acetic acid or a sulfonic acid in such an amount, until a pH-value in the range from 4.3 to 4.4 is obtained, whereby the crystallization of (6S)—N(5)-methyl-5,6,7,8-tetrahydrofolic acid of the Formula IV

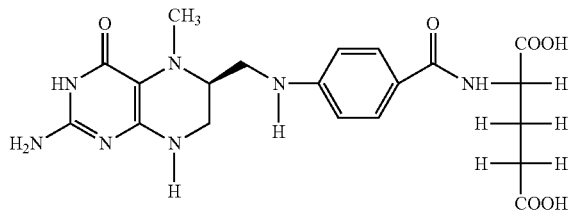

Formula IV begins, and whereby during this crystallization the pH-value is maintained in the range from 4.3 to 4.4 by continuous addition of either acetic acid or of a sulfonic acid;

(d) filtering off crystalline (6S)—N(5)-methyl-5,6,7,8-tetrahydrofolic acid of the Formula IV at a temperature in the range from 44° C. to 46° C.;

(e) isolating (6S)—N(5)-methyl-5,6,7,8-tetrahydrofolic acid of the Formula IV;

(f) suspending the (6S)—N(5)-methyl-5,6,7,8-tetrahydrofolic acid of the Formula IV of step (e) in water at a temperature from 35° C. to 41° C.;

(g) continuously adding a sodium hydroxide solution to the aqueous suspension containing (6S)—N(5)-methyl-5,6,7,8-tetrahydrofolic acid of the Formula IV of step (f) to adjust the pH to a range from 6.7 to 6.9;

(h) adding 0.90 equivalents of calcium chloride to the solution of step (g) with respect to each equivalent of (6S)—N(5)-methyl-5,6,7,8-tetrahydrofolic acid of the Formula IV;

(i) adjusting the concentration of the compound of Formula IV in the resulting mixture of step (h) to a value in the range from 14% by weight to 16% by weight by the addition or by removal of water;

(j) starting the precipitation of the calcium salt of (6S)—N(5)-methyl-5,6,7,8-tetrahydrofolic acid of the Formula V from the mixture of step (i) by the addition of a small amount of previously prepared compound of Formula V;

(k) maintaining the mixture of step (j) at a temperature of 40° C. for one hour;

(l) lowering the temperature of the mixture of step (k) from 40° C. to a temperature of 23° C. over two hours;

(m) maintaining the mixture of step (l) at 23° C. for a period of 16 hours to 18 hours; and (n) isolating the amorphous calcium salt of (6S)—N(5)-methyl-5,6,7,8-tetrahydrofolic acid of the Formula V from the mixture of step (m), wherein the calcium chloride is added as a solid or an aqueous solution.

* * * * *